(12) United States Patent
Kostelnicek et al.

(10) Patent No.: US 6,272,915 B1
(45) Date of Patent: Aug. 14, 2001

(54) DUAL TRANSMITTER MULTI-CAPACITANCE FLOW METER

(75) Inventors: Richard J. Kostelnicek, Dickinson; Peter W. Reittinger, Katy, both of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/298,680

(22) Filed: Apr. 23, 1999

(51) Int. Cl.[7] .............. E21B 47/04; E21B 49/00; G01N 27/22; G01N 33/00
(52) U.S. Cl. ............ 73/152.28; 73/61.44; 73/152.55; 73/152.18; 324/664; 324/694; 324/698; 166/250.03
(58) Field of Search ............... 73/152.28, 61.44, 73/152.55, 152.31, 152.18; 324/689, 694, 698, 664; 166/264, 250.03

(56) References Cited

U.S. PATENT DOCUMENTS

| | | | |
|---|---|---|---|
| 2,517,603 | * | 8/1950 | Silverman ............... 73/155 |
| 3,176,511 | * | 4/1965 | Widmyer ............... 73/155 |
| 3,721,121 | * | 3/1973 | Fierfort ............... 73/155 |
| 3,942,374 | * | 3/1976 | Glenn et al. ............... 73/155 |
| 4,015,194 | * | 3/1977 | Epling ............... 324/1 |
| 4,441,362 | * | 4/1984 | Carlson ............... 73/155 |
| 5,070,725 | * | 12/1991 | Cox et al. ............... 73/61.1 R |
| 5,132,903 | * | 7/1992 | Sinclair ............... 364/422 |
| 5,239,862 | * | 8/1993 | Atkinson ............... 73/64.44 |
| 5,249,455 | * | 10/1993 | Cox ............... 73/61.44 |
| 5,260,667 | * | 11/1993 | Garcia-Golding et al. ...... 324/694 |
| 5,417,107 | * | 5/1995 | Biencourt et al. ............... 73/61.44 |
| 5,736,637 | * | 4/1998 | Evans et al. ............... 73/152.31 |

\* cited by examiner

Primary Examiner—Hezron Williams
Assistant Examiner—David J. Wiggins

(57) ABSTRACT

A system for evaluating multiphase fluid flow in a wellbore. Two distinct AC signals are injected into a fluid. One AC signal originates from a transmitter electrode in ohmic contact with the fluid, and the other AC signal originates from a transmitter electrode capacitively coupled to the fluid. The geometric factors between the electrode pairs are selected to distinguish between different constituents within the wellbore fluids. The output electrical impedance of the ohmic transmitter is low so that the AC signal from the capacitive transmitter is shunted to signal ground in electrically conductive fluids. A single detector can measure the fraction of electrically conductive water covering the detector electrode as well as the dielectric constant of an oil and gas mixture. Arrays of such detector electrodes can measure the holdups and velocities of the constituent fluids in a flowing multiphase fluid.

20 Claims, 2 Drawing Sheets

DUAL TRANSMITTER MULTI-CAPACITANCE FLOW METER

BACKGROUND OF THE INVENTION

The present invention relates to the downhole evaluation of formation fluids produced into a wellbore. More particularly, the invention relates to a real-time downhole multiphase flow evaluation apparatus and method which distinguishes capacitive and conductive fluids by exciting the fluids with distinct transmitters.

Wellbores are drilled into earth formations to produce hydrocarbon fluids from subsurface reservoirs. The formation fluids are produced at changing flowrates and comprise varying mixtures of hydrocarbons and water. Efficient production of hydrocarbons requires information regarding the production flowrates from specific locations within the wellbore, and the quantity of water produced with the hydrocarbon fluids. Production logging tools measure the instantaneous relative quantity ("holdup") and instantaneous velocity of the formation fluids in the wellbore as a function of time and location in the wellbore.

Logging tools have used capacitance sensors to evaluate formation fluids downhole in wellbores. A capacitance sensor comprises a transmitter electrode and a detector electrode oriented in a selected geometry. Capacitance sensors measure small changes in materials, typically resulting from impurities in the materials. If two capacitance sensors are separated by a known distance and the responses of the sensors to perturbations in a flowing medium can be correlated, the velocity of the medium can be calculated. Additionally, the magnitude of the electrical current traveling from the transmitter to the detector is proportional to the electrical admittance of the medium occupying the volume between these electrodes. Because hydrocarbons are essentially nonconductive and have an electrical permittivity twice that of air, hydrocarbons have a very low admittance particularly exacerbated by low measurement frequencies. Conversely, reservoir produced water is at least moderately saline and has a correspondingly high admittance.

In production logging of formation fluids, the electrical admittance of the formation fluids can vary more than six orders of magnitude. Although tools have been proposed to measure fluid velocities and holdups with capacitance sensor arrays, such systems do not provide satisfactory performance as a production logging tool.

One method and apparatus for measuring multiphase properties with a capacitance sensor array was described in European Patent Application No. 0510774A2 to DenBoer, wherein a plurality of capacitors were positioned vertically in a pipeline by placing a single electrode on one side of the fluid sample, and a segmented electrode on the other side of the fluid. Higher placed electrode segments identified the fluid level in the pipeline, and lower placed electrode segments measured the impedance of the liquid. The fraction of water in the liquid-filled part of the pipeline was determined by calculating the effective dielectric constant of the fluid from the capacitor impedance measurement, and was based on the theoretical relationship between the effective dielectric constant of an oil/water mixture and the ratio of oil in the water.

This system is not effective as a production logging tool because capacitance sensors have a very high input impedance and are susceptible to stray capacitance. When a metallic tool body and a capacitance sensor are immersed in an electrically conductive fluid there will be stray capacitance between the sensor and the tool electronics. For a production logging tool which must operate downhole in a wellbore, elimination of stray capacitance between tool electronics and metallic tool housings is difficult to accomplish.

Downhole sensor arrays have been constructed to measure the velocity and holdup of constituent fluids in a flowing multiphase fluid, however a single sensor does not provide stable and accurate results in both electrically conductive and nonconductive fluids. For an alternating current at a selected frequency, the electrical admittance of a fluid is a function of the conductivity, permittivity, and geometry of the fluid. Admittance comprises the reciprocal of impedance, and is measured as a ratio of current to voltage. At frequencies less than 10 megahertz, the admittance of moderately saline Water essentially comprises a conductance and the admittance of oil and gas essentially comprises a capacitance. At these lower frequencies, the conductive admittance of waters found in a wellbore is typically many orders of magnitude greater than the capacitive admittance of oil and gas, and the capacitance of oil is only twice that of gas. The magnitude of the current detected by one sensor will be proportional to the magnitude of the fluid electrical admittance between a transmitter electrode and the sensor. Accordingly, a single sensor that spans the range of admittance in the fluids of interest will have a limited resolution.

U.S. Pat. No. 5,736,637 to Evans et al. (1998) disclosed a system for evaluating multiphase flow downhole with a production logging tool. An array of capacitance sensors was combined with an array of conductivity sensors, and the mutually exclusive-outputs were multiplexed. This concept doubles the number of sensors and space required for containing measurement electronics. Construction of such a system is difficult to accomplish in logging tools small enough to traverse a wellbore. Additionally, the construction of conductance sensors in proximity to capacitance sensors inevitably creates stray capacitances which will degrade the capacitance measurement.

A need exists for an improved downhole sensor which can efficiently provide stable and accurate multiphase fluid evaluation in a wellbore as the fluid electrical conductivity and flow rate changes. The system should provide high measurement resolution while traversing the narrow confines of a wellbore and should withstand elevated wellbore temperatures and pressures.

SUMMARY OF THE INVENTION

The invention provides an apparatus and method for evaluating multiphase fluid downhole in a wellbore. The apparatus comprises a housing insertable in the wellbore at a desired downhole position, an ohmic transmitter electrode in contact with the fluid and having a low output electrical admittance, a capacitive transmitter electrode in contact with the fluid and having a high output electrical impedance, a detector electrode in contact with the fluid and having a high input impedance. A generator is engaged with said housing and with the ohmic transmitter electrode and with the capacitive transmitter electrode for selectively charging the transmitter electrodes with electrical charges, and a controller is engaged with the generator and with the detector electrode for determining the electrical charges transmitted from the generator to the ohmic transmitter electrode and to the capacitive transmitter electrode, for determining the electrical charges detected by the detector electrode, and for evaluating the multiphase fluid based on such electrical charges.

The method of the invention comprises the steps of placing a housing in a wellbore, placing an ohmic transmitter electrode and a capacitive transmitter electrode and a detector electrode in contact with the fluid, of flowing the fluid through the housing chamber, of selectively providing electricity to the ohmic transmitter electrode and to the capacitive transmitter electrode, of operating the detector electrode to detect electricity transmitted through the fluid by the transmitter electrodes, and operating a controller to determine the electricity transmitted to the fluid by the ohmic transmitter electrode and by the capacitive transmitter electrode, to determine the electricity detected by the detector electrode, and to evaluate the multiphase fluid. The controller can be operated to determine the fluid flowrate between the electrodes and to determine the fluid composition.

DESCRIPTION OF THE PREFERRED EMBODIMENTS

The invention provides a system for measuring multiphase fluid flow rates in a wellbore by evaluating the relative admittance of a flowing fluid. The invention resolves the limited resolution problem of prior art sensors by detecting electrical charges from two distinct transmitters operating through different transmission paths. The presence of substantially nonconductive hydrocarbons such as oil and gas is detected primarily from a capacitive electrode paired with a detector electrode, and the presence of conductive water is detected primarily from an ohmic transmitter electrode paired with a detector electrode.

Figure 1:
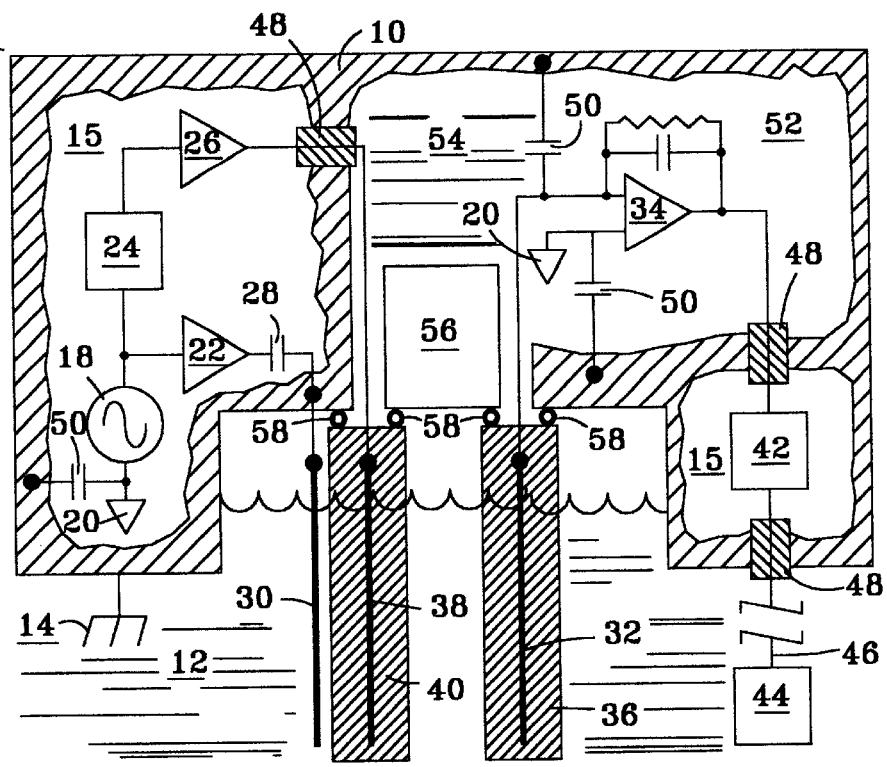
FIG. 1 illustrates a block diagram of a multiphase evaluation tool having an ohmic transmitter electrode, a capacitive transmitter electrode, and a detector electrode.

FIG. 1 illustrates a schematic view for one embodiment of the invention. Housing 10 is electrically conductive and can be configured to enclose other components as described below. Housing 10 is positioned within a cased or uncased wellbore in contact with formation fluids 12, and can be located within a vertical, inclined, or horizontal wellbore section. Earth ground 14 represents the electrical potential of formation fluids 12, and this potential is transferred to housing 10 through direct contact with formation fluids 12. Housing 10 encloses a sealed interior space defined as atmospheric cavity 16 for containing various electronics at atmospheric pressure. The pressure of formation fluids 12 will typically exceed the pressure within atmospheric cavity 16 by a significant amount.

AC generator 18 can be positioned within atmospheric cavity 15 to produce an alternating electric current having signal ground 20. As shown in FIG. 1, a portion of the AC current is conducted directly to buffer amplifier 22, and the remainder of the current is delayed one forth of a period, or 90 degrees, by phase delay circuit 24 before such current is transmitted to buffer amplifier 26. The output from amplifier 22 is AC coupled to housing 10 through very low electrical impedance 28 and is transmitted to ohmic transmitter electrode 30. As representative examples, the frequency of the AC current can comprise 66.5 kHz, the low impedance 28 can comprise a 2 microfarad capacitor, and the magnitude of the AC signal can comprise approximately one volt. Ohmic transmitter electrode 30 contacts formation fluids 12 to transmit the AC electrical charge to fluids 12.

Ohmic transmitter electrode 30 comprises an electrically conductive material in direct contact with wellbore fluids 12. AC current flows between ohmic transmitter electrode 30 and detector electrode 32 maintained virtually at signal ground 20 by detector amplifier 34. Detector electrode 32 is encased in an electrically nonconductive material 36 which makes the electrical coupling between detector electrode 32 and wellbore fluid 12 capacitive in nature. The capacitively coupled detector electrode 32 is connected to detector amplifier 34 in a configuration comprising a charge coupled amplifier. The thickness of nonconductive material 36 is minimized to maximize the sensitivity of detector amplifier 34 to changes in wellbore fluid 12. Similarly, capacitive transmitter electrode 38 is encased in nonconductive material 40.

Capacitive transmitter electrode 38 comprises an electrically conductive material which is AC coupled to wellbore fluid 12 through nonconductive material 40. The thickness of nonconductive material 40 should be minimized to minimize the impedance between capacitive transmitter electrode 38 and wellbore fluids 12, however this thickness is less critical than the thickness of nonconductive material 36 covering detector electrode 32. As representative examples, nonconductive materials 36 and 40 can comprise a polyimide film less than 0.005 inches thick, and capacitive transmitter electrode 38 and detector electrode 32 can be constructed as internal conductive layers on separate printed circuit boards.

In a preferred embodiment of the invention, nonconductive material 40 covering capacitive transmitter electrode 38 creates an electrical impedance to current flow which is greater than low output impedance 28 in series with ohmic transmitter electrode 30. Similarly, nonconductive material 36 covering detector electrode 32 creates a high electrical impedance to current flow. The impedance of said electrodes is in series with the admittance of formation fluids 12, and current will flow through a path to signal ground which minimizes these impedances and maximizes this admittance. As a representative example, low output impedance 28 for ohmic electrode 30 can comprise a 2.0 microfarad capacitance, the output impedance for capacitive transmitter electrode 38 is a 0.004 microfarad capacitance, and the input impedance for detector electrode 32 is a 50.0 picofarad capacitance.

The relative positioning of ohmic transmitter electrode 30, capacitive transmitter electrode 38, and detector electrode 32 is important to the proper operation of the invention. Ohmic transmitter electrode 30, capacitive transmitter electrode 38, and detector electrode 32 are positioned in contact with formation fluids 12. The relative positioning and dimensions of each electrode pair is described quantitatively with a single term defined herein as a "geometric factor". The geometric factor is directly proportional to the area of the electrodes and inversely proportional to the electrical length between electrodes. For a pair of electrodes, at a given frequency, in a medium having given electrical properties such as conductivity and permittivity, the electrical admittance between the electrodes is directly proportional to the geometric factor of the electrodes. This relationship is important because the quantity of current transmitted is determined by the product of the medium's conductivity or permittivity times the geometric factor.

In a preferred embodiment of the invention, the geometric factor of capacitive electrode 38 with detector electrode 32 is greater than the geometric factor of ohmic electrode 30 with detector electrode 32. Similarly, the geometric factor of capacitive electrode 38 with detector electrode 32 is greater than the geometric factor of capacitive electrode 38 with ohmic electrode 30. These geometric factors in combination with the electrode impedances described above have the effect of changing the current flow patterns as the admittance of formation fluid 12 changes. For example, in oil and gas which have a relatively small capacitive admittance, more current will flow to detector electrode 32 from capacitive electrode 38 than from ohmic electrode 30 because of the limiting geometric factor of ohmic electrode 30 with detector electrode 32. In water, which has a relatively large conductive admittance, current will flow from capacitive electrode 38 to ohmic electrode 30 because of low output impedance 28, and the current flowing to detector electrode 32 from ohmic electrode 30 will increase because of the increased; admittance of the water. As a consequence of this method, the dynamic range of the quantity of current measured by detector electrode 32 can be significantly less than the dynamic range of the admittance of formation fluid 12, without sacrificing resolution at the extremes of the admittance.

In one embodiment of the invention as shown in FIG. 1, capacitive transmitter electrode 38 and detector electrode 32 form a parallel plate capacitor. Ohmic transmitter electrode 30 comprises a plate shielded by capacitive transmitter electrode 38 relative to detector electrode 32. In this position capacitive transmitter electrode 38 shields detector electrode 32 from ohmic transmitter electrode 30. This shielding has the effect of increasing the electrical path from ohmic electrode 30 to detector electrode 32, thereby decreasing the geometric factor for this electrode pair. Similarly, the electrical length from the surface of capacitive electrode 38 which faces detector electrode 32, to detector 32, is less than the electrical length from said surface to ohmic electrode 30. In fluids such as oil and gas having a small electrical admittance, the AC current measured by detector amplifier 34 is predominantly from capacitive transmitter electrode 38. In fluids such as water having a large electrical admittance, the AC current measured by detector amplifier 34 is predominantly from ohmic transmitter electrode 30.

In one embodiment of the invention as shown in FIG. 1, signal processing electronics 42 performs in-phase and quadrature detection on the output from detector amplifier 34. As a result of nonconductive material 36 surrounding detector electrode 32, the phase delay from any transmitter electrode to detector amplifier 34 of any particular AC current will be essentially the same for conductive and capacitive formation fluid 12. In nonconductive formation fluid 12, electrical current will be delayed by the capacitance of formation fluid 12. In conductive formation fluid 12, current flow will be delayed by the capacitance of nonconductive material 36. The AC current at capacitive transmitter electrode 38 is delayed by 90 degrees relative to the AC current at ohmic transmitter electrode 30 because of phase delay circuit 24. In phase and quadrature detection by signal processing electronics 42 discriminates between the magnitude of the AC current from ohmic transmitter electrode 30 and the magnitude of the AC current from capacitive transmitter electrode 38. The processed signals are converted to an appropriate format and conducted to surface electronics 44 where all data is archived and displayed.

In a borehole, formation fluids 12 are at pressures greater than atmospheric pressure. The transmitter and detector electrodes are exposed to the pressure of formation fluid 12 while the electronics in atmospheric cavities 15 are maintained at atmospheric pressure. Conductor 46 for carrying data from signal processing electronics 42 to surface electronics 44 is also exposed to formation fluid 12 pressures. High pressure electrical feedthrough 48 permits electrical signals to be conducted through housing 10 with electrical isolation from housing 10. Accordingly, stray capacitance 50 exists between housing 10 and signal ground 20 as well as between housing 10 and the input of detector 34. To minimize these stray capacitances 50 so that the relatively small capacitances of oil and gas fluids can be measured, detector amplifier 34 can be mounted directly to a printed circuit board on which detector electrode 32 is constructed as an internal conducting layer. Detector amplifier 34 is housed in a pressure compensated cavity 52 filled with an electrically and chemically inert fluid 54. A suitable fluid which is relatively incompressible is, Dow Corning 200 silicon fluid. Pressure compensation mechanism 56 maintains a pressure differential less than several psi between formation fluid 12 and pressure compensated cavity 52. O-ring seals 58 between housing 10 and interior of cavity 52 are sufficient to keep chemically reactive and electrically conductive formation fluids 12 out of pressure compensated cavity 52. High pressure feedthrough 48 permits electrical signals to be conducted between atmospheric cavity 15 and pressure compensated cavity 52.

Detector amplifier 34 measures any spurious AC currents on housing 10 through stray capacitance 50 to detector 34 input. This stray capacitance can be minimized. However, when formation fluid 12 is electrically conductive, any spurious signal on housing 10 will be measured through the larger capacitance of detector electrode 32. Driving housing 10 with an AC signal through the low output impedance of buffer amplifier 22 effectively shunts to signal ground 20 any spurious AC currents. Similarly, in conductive formation fluids 12, the AC from capacitive transmitter electrode 38 will be shunted to signal ground 20 by housing 10 and also by ohmic transmitter electrode 30. The freshest water downhole in a wellbore is sufficiently saline to provide the conductivity required for operation of the invention. In water, the AC current measured by detector amplifier 34 will have originated from buffer amplifier 22 and will not have been delayed by phase delay circuit 24. In electrically nonconductive formation fluids such as oil and gas, a portion of the AC current from capacitive transmitter electrode 38 will be measured by detector amplifier 34. If detector electrode 32 is sufficiently shielded from ohmic transmitter electrode 30 by capacitive transmitter electrode 38, the geometric factor of this electrode pair will be small, and there will be little or no current from ohmic transmitter electrode 30 measured by detector amplifier 34 in oil and gas. The AC current from capacitive transmitter electrode 38 originates from buffer amplifier 26 and is time delayed one quarter of a period relative to the AC current from ohmic transmitter electrode 30. Signal processing electronics 42 convert the output of detector amplifier 34 into two separate outputs including an in-phase output and a quadrature output. This signal processing can exploit the orthogonality of the AC currents from the two transmitter electrodes such that the magnitude of the current in oil and gas becomes the quadrature output, and the magnitude of the current in water is measured as the in-phase output.

Figure 2:
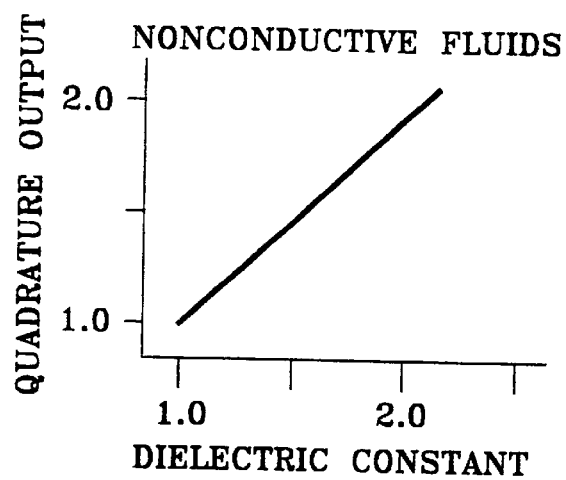
FIG. 2 illustrates the quadrature outputs in nonconductive fluids as a function of the fluid dielectric constant.

If the capacitance of a nonconductive formation fluid 12 is small compared to the capacitance of nonconductive materials 36 and 40, then the current measured by detector amplifier 34 will be directly proportional to the dielectric constant or relative permittivity of the fluid 12. FIG. 2 illustrates the quadrature outputs from one embodiment of the invention as the dielectric constant of a nonconductive fluid increases from 1.0 in air or gas to the 2.1–2.5 range typically measured for oils. The quadrature output increases as ailinear function of the dielectric constant of fluid 12. This relationship permits the oil and gas holdups to be calculated from the quadrature output, which indicates the bulk dielectric constant for a parallelepiped volume between capacitive transmitter electrode 38 and detector electrode 32. In a representative example detector electrode 32 and capacitive transmitter electrode are approximately 0.5 inch square and covered with a polyimide film less than 0.005 inches thick. Ohmic transmitter electrode 30 is located behind capacitive transmitter electrode 38 and the gap between such capacitive transmitter electrode 38 and detector electrode 32 is approximately 0.4 inches. For an apparatus with these dimensions the quadrature output is a linear function of dielectrid constant in the range of 1.0 to 2.5. Therefore, the quadrature output can be calibrated in units of dielectric constant with two measurements in fluids having known and different dielectric constants within this range.

Figure 3:
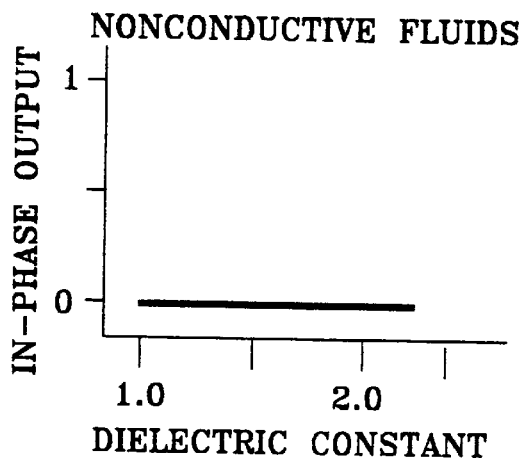
FIG. 3 illustrates the in-phase output in nonconductive fluids as a function of the fluid dielectric constant.

FIG. 3 illustrates the in-phase output when the sensors are immersed in a nonconductive fluid as the dielectric constant of the fluid increases from 1.0 to 2.5. Current from ohmic electrode 30 is too small to be detected because of the small geometric factor between this electrode and detector electrode 32 and the low admittance of the nonconductive fluid.

Figure 4:
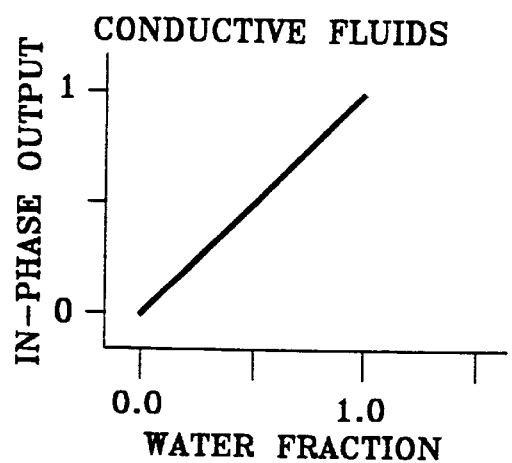
FIG. 4 illustrates the in-phase output in conductive fluids as a function of the fraction of the sensor area covered with conductive water.

FIG. 4 illustrates the in-phase output as transmitter electrodes 30 and 38 and detector electrode 32 are immersed in water having a conductivity greater than 1.0 Siemens/meter. The ratio of the water covered area of detector electrode 32 to the total area of detector electrode 32 comprises the water fraction as illustrated. This in-phase output is a linear function of this water fraction and the scale for the in-phase output is derived from two measurements (1) when detector electrode 32 is in air, and (2) when detector electrode 32 is submerged in water.

Multiple doctor electrodes 32 can be positioned in arrays as described in U.S. Pat. No. 5,736,637, incorporated herein by reference, for the purpose of measuring holdups and velocities across the dimensions of a wellbore.

In another embodiment of the invention, the signals for transmitter electrodes 30 and 38 can comprise orthogonal continuous wave signals. A single detector electrode 32 measures the combined signals, and the output from the detector electrode 32 is processed by electronics capable of discriminating between the two transmitted signals.

In another embodiment of the invention, the signals for the two transmitter electrodes can be AC signals having two different frequencies. A single detector electrode 32 measures the combined signals, and the output from detector electrode 32 will be processed by electronics capable of discriminating between the two detector output frequencies.

Figure 5:
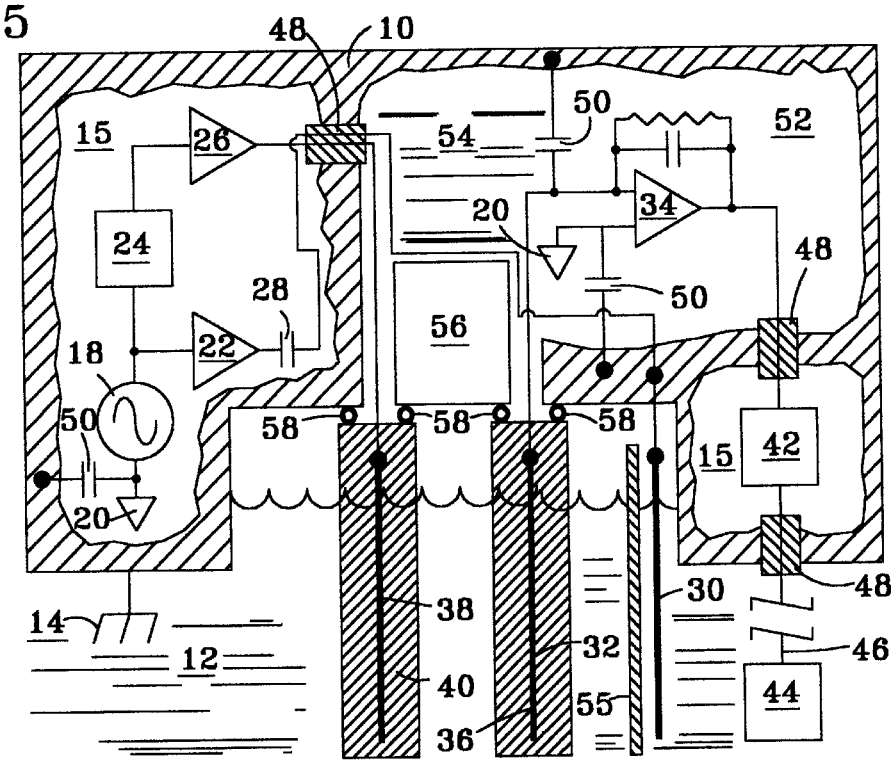
FIG. 5 illustrates a shield between an ohmic electrode and a detector electrode.

FIG. 5 illustrates another embodiment of the invention wherein ohmic electrode 30 is positioned at another location relative to detector electrode 32. Shield 55 is positioned between ohmic electrode 30 and detector electrode to modify the conductance therebetween. The size and effectiveness of shield 55 can be modified, and the distance between detector electrode 32 and ohmic electrode 30 can be varied to accomplish the desired result.

The output from the capacitive transmitter can be increased to improve the resolution between oil and gas without adversely affecting the sensor's response in water. The ohmic electrode shunts to ground currents from the capacitive electrode and elsewhere, thereby making the sensor less susceptible to stray capacitances and spurious signals. An array of sensors with dual transmitters is capable of distinguishing between oil, gas, and water with sufficient resolution to make the holdup and velocity measurements necessary to calculate constituent flow rates of a three-phase formation fluid.

The invention is particularly suitable for logging tools, and is particularly useful in deviated or horizontal wellbores where the formation fluids are found in multiple phase conditions within the same wellbore. The invention can be temporarily run in the wellbore as a logging tool, or can be positioned downhole in a wellbore to evaluate the formation fluids over a long period of time. Operation of the invention substantially reduces the negative impact of stray capacitances on detectable measurements.

The operation of surface electronics 44 can be performed at the surface or downhole within the wellbore. Similarly, generator 18 can be located downhole within housing 10 or can be located at the surface with engagement with housing 10 through an electrical conductor (not shown). Ohmic electrode 30 can be located at different positions relative to detector electrode 32, and the inverse relationship regarding the distance selected between such electrodes can be correlated to the characteristics of formation fluids 12.

Although the invention has been described in terms of certain preferred embodiments, it will be apparent to those of ordinary skill in the art that modifications and improvements can be made to the inventive concepts herein without departing from the scope of the invention. The embodiments shown herein are merely illustrative of the inventive concepts and should not be interpreted as limiting the scope of the invention.

What is claimed is:

1. An apparatus for evaluating multiphase fluid downhole in a wellbore, comprising:
    a housing insertable in the wellbore at a desired downhole position;
    an ohmic transmitter electrode in contact with the fluid and having a low output admittance;
    a capacitive transmitter electrode in contact with the fluid and having a high output impedance;
    a detector electrode in contact with the fluid and having a high input impedance;
    a generator engaged with said housing and connected with said ohmic transmitter electrode and with said capacitive transmitter electrode for selectively charging said transmitter electrodes with electrical charges simultaneously; and
    a controller engaged with said generator and with said detector electrode for determining the electrical charges transmitted from said generator to said ohmic transmitter electrode and to said capacitive transmitter electrode, for determining the electrical charges detected by said detector electrode, said determinations being substantially simultaneous, and for evaluating the multiphase fluid based on such electrical charges.

2. An apparatus as recited in claim 1, wherein said determinations are based at least in part on a geometric factor of said capacitive transmitter electrode with said detector electrode and a geometric factor of said ohmic transmitter electrode with said detector electrode.

3. An apparatus as recited in claim 1, wherein said detector electrode is shielded from said ohmic transmitter electrode.

4. An apparatus as recited in claim 3, wherein said capacitive transmitter is positioned within said fluid to shield said detector electrode from said ohmic transmitter electrode.

5. An apparatus as recited in claim 1, wherein said generator transmits different frequencies to said ohmic transmitter electrode and to said capacitive transmitter electrode, and said controller is capable of distinguishing between the different frequencies measured by said detector electrode.

6. An apparatus as recited in claim 1, wherein said generator transmits continuous wave electrical signals to said ohmic transmitter electrode and to said capacitive transmitter electrode, said signals being orthogonal, and wherein said controller is capable of distinguishing between said orthogonal electrical signals.

7. An apparatus as recited in claim 1, wherein said generator is located at a distance from said housing and is engaged with said housing with an electrical conductor.

8. An apparatus as recited in claim 1, further comprising at least two detector electrodes positioned at different elevations within said wellbore to distinguish different fluid levels within said wellbore.

9. An apparatus for evaluating multiphase fluid downhole in a wellbore, comprising:
    a housing insertable in the wellbore at a desired downhole position;
    an ohmic transmitter electrode in contact with the fluid and having a low output impedance;
    a capacitive transmitter electrode in contact with the fluid and having a high output impedance;
    a detector electrode in contact with the fluid and having a high input impedance;
    a generator engaged with said housing and connected with said ohmic transmitter electrode and with said capacitive transmitter electrode for selectively and simultaneously charging said transmitter electrodes with electrical charges, wherein said generator includes a phase delay circuit for delaying the electrical charges transmitted to said capacitive transmitter electrode; and
    a controller engaged with said generator and with said detector electrode for determining the electrical charges transmitted from said generator to said ohmic transmitter electrode and to said capacitive transmitter electrode, for determining the electrical charges detected by said detector electrode, said determinations being substantially simultaneous, and for evaluating such electrical charges to determine the composition of water and hydrocarbons within the fluid.

10. An apparatus as recited in claim 9, wherein said determinations are based at least in part on a geometric factor of said capacitive transmitter electrode with said detector electrode and a geometric factor of said ohmic transmitter electrode with said detector electrode.

11. An apparatus as recited in claim 9, wherein said controller is positioned within a sealed interior space within said housing and is electrically grounded to said housing.

12. An apparatus as recited in claim 9, wherein said generator is positioned within a sealed interior space within said housing and is electrically grounded to said housing.

13. An apparatus as recited in claim 9, further comprising at least two detector electrodes positioned at different elevations within said wellbore to distinguish different fluid levels within said wellbore.

14. A method for evaluating multiphase fluid downhole in a wellbore, comprising the steps of:
    placing a housing in a wellbore so that an ohmic transmitter electrode, a capacitive transmitter electrode, and a detector electrode contact the fluid;
    flowing the fluid around said electrodes;
    selectively providing electricity simultaneously to said ohmic transmitter electrode and to said capacitive transmitter electrode;
    operating said detector electrode to simultaneously detect electricity transmitted through the fluid by said transmitter electrodes; and
    operating a controller to determine the electricity transmitted to the fluid by said ohmic transmitter electrode and by said capacitive transmitter electrode, to determine the electricity detected by said detector electrode, and to evaluate the multiphase fluid.

15. A method as recited in claim 14, further comprising the step of operating said controller to determine the flow rate of the fluid around said electrodes.

16. A method as recited in claim 14, further comprising the step of operating said controller to determine the composition of the fluid.

17. A method as recited in claim 14, further comprising the step of orthogonalizing the electricity provided to said ohmic transmitter electrode and to said capacitive transmitter electrode.

18. A method as recited in claim 14, further comprising the step of providing electricity at different frequencies to said ohmic transmitter electrode and to said capacitive transmitter electrode.

19. A method as recited in claim 14, where said wellbore fluid has an admittance and the electricity detected by said detector electrode is in the form of a current, said current having a dynamic range less than a dynamic range of the wellbore fluid admittance.

20. A method as recited in claim 14, wherein said determinations are based at least in part on a geometric factor of said capacitive transmitter electrode with said detector electrode and a geometric factor of said ohmic transmitter electrode with said detector electrode.

* * * * *